US00PP09674P

United States Patent [19]

Drewlow

[11] Patent Number: Plant 9,674

[45] Date of Patent: Oct. 29, 1996

[54] KALANCHOE PLANT NAMED CHIVALRY

[75] Inventor: .yndon W. Drewlow, Ashtabula, Ohio

[73] Assignee: Mikkelsens, Inc., Ashtabula, Ohio

[21] Appl. No.: 490,013

[22] Filed: Jun. 13, 1995

[51] Int. Cl.[6] ..... A01H 5/00

[52] U.S. Cl. ..... Plt./87.15

[58] Field of Search ..... Plt./87.15

*Primary Examiner*—James R. Feyrer

*Attorney, Agent, or Firm*—Foley & Lardner

[57] ABSTRACT

A new Kalanchoe cultivar named Chivalry characterized by the combined features of salmon pink flower color, early flowering time, compact plant habit, floriferous habit, good keeping quality, and excellent basal branching.

1 Drawing Sheet

The present invention relates to a new and distinct cultivar of Kalanchoe plant, botanically known as *Kalanchoe blossfeldiana,* and referred to by the cultivar name Chivalry.

The new cultivar was discovered by the inventor Lyndon W. Drewlow in Ashtabula, Ohio, as a spontaneous mutation of the cultivar Majestic, disclosed in U.S. Plant Pat. No. 7,794. Chivalry was noted primarily due to its salmon pink flower color. compared to the scarlet rose flower color of Majestic.

Asexual reproduction by stem cuttings taken by the inventor in Ashtabula, Ohio has shown that the unique features of Chivalry are stabilized and are reproduced true to type in successive propagations.

The following characteristics distinguish Chivalry from both its parent variety and other cultivated Kalanchoes of this type known and used in the floriculture industry. The characteristics are described with comparative reference to Majestic and the cultivar Citation, disclosed in U.S. Plant Pat. No. 5,533.

1. Chivalry has salmon pink (39A to 39B) flowers which are a lighter salmon pink than Citation (52B) and clearly different from the scarlet rose (45B) color of Majestic.

2. Flowering time for Chivalry is 4 to 7 days earlier than Citation under summer conditions and 10 to 14 days earlier under winter conditions. The flowering time of Chivalry is similar to Majestic.

3. Average flower diameter of Chivalry is 15 mm, similar to Majestic but larger than the 12 to 13 mm diameter of Citation.

4. Average height of Chivalry is 15 to 18 cm under winter conditions, similar to Majestic but shorter than Citation which is 20 to 22 cm.

5. Keeping quality of individual flowers of Chivalry is 3 to 5 days longer than Citation. The length of time plants of Chivalry stay in flowers after short day treatment is 1 to 2 weeks longer than Citation and similar to Majestic.

6. Leaf color and size are similar for all three cultivars. However, Citation has deeper cut crentions than Chivalry and Majestic, and there is more lobing in the leaf of Citation.

7. Internodes, peduncles and pedicles of Chivalry are up to 5 mm shorter than Citation on a comparable stem.

8. In Chivalry and Majestic, the lower branches tend to grow outward and not as long as the main stem and upper branches present a mounded appearance. In Citation, all branches and the main stem finish at the same height resulting in an upright growing plant with flowers on the top.

9. Total number of flowers in the inflorescence of Chivalry is up to double the number in the Citation inflorescence due to more branching and more flowers on each branch.

The accompanying color photograph is a top perspective view illustrating the overall appearance of Chivalry showing the colors as true as it is reasonably possible to obtain in a color reproduction of this type. The photograph was taken on Mar. 31, 1995 under natural light on an overcast day under a ridged plastic greenhouse covering at Ashtabula, Ohio.

The following is a detailed description of the new cultivar, based on plants produced in greenhouses in Ashtabula, Ohio during the winter season of the year. Plants were grown in 10 cm pots and measurements were taken 16 weeks after rooted cuttings were planted. Height measurements were taken from the soil line of the container. The plants were grown at 65° to 68° F. night temperatures under 3500 to 4000 foot candles of light, and with nutritional levels on 175 ppm Nitrogen, 75 ppm Potassium, and 175 PPM Phosphorous, with trace elements added. Habit of growth, plant height, flowering time, size of leaves and peduncle length wiil be influenced by nutritional and environmental conditions.

Color references are made to The Royal Horticultural Society Colour Chart except where general terms of ordinary dictionary significance are used.

Classification:

*Commercial.*—*Kalanchoe blossfeldiana* cv. Chivalry.

Parentage: Spontaneous mutation of Majestic, disclosed in U.S. Plant Pat. No. 7,794.

Propagation:

*Type cutting.*—Stem tip cutting up to 3 cm long.

*Time to root.*—10 days at 21° C. summer, 14 days at 21° C. Winter.

*Rooting habit.*—Fine, fibrous, abundant.

*Habit and form of Growth.*—Compact, flower clusters are held above foliage; excellent basal branching results in mounded growth habit. Environment and use of growth regulators will play a role in final height.

*Foliage.*—Leaves are simple and opposite. Size: Average full grown leaves on a plant when grown in a 10 cm pot are 8 to 9 cm long and 5 to 6 cm wide. Shape: Ovate, apex obtuse, base rounded. Texture: Glabrous, coriaceous and succulent. Margin: Crenate, shallow lobed. Color: Young foliage, top side 146A, under side 146B; mature foliage, top side 147A, under side 147B.

Flowering description:

*Flowering habits.*—The inflorescence is a compound dichasial cyme. Terminal flower on main axis opens first, followed by the terminal flowers of the side branches, continuing with the subsequent development of branches in the inflorescence. Inflorescence is made up of the main stem and up ten lateral branches.

*Natural flowering season.*—Early January Flowering time under controlled daylength at 20° C. in summer is 10 weeks, and in Winter is 11½ weeks. Flowering time depends on temperature, light intensity and other growing conditions.

*Flower buds.*—Oblong, up to 7 mm long before showing color, developing tubular as flower petals mature; sheathed in four (4) green sepals.

*Flowers borne.*—Compound dichasial cymes. Primary peduncle 4 mm in diameter just below the first branch of the inflorescence; length will vary depending on growing conditions. Pedicels vary in length depending on where they are located in inflorescence.

*Quantity of flowers.*—Very floriferous with main stem and up to 10 lateral branches each having from 30 to 50 or more flowers.

*Petals.*— Shape: Almost rounded, top cuspidate. Color: Top side when opening 39A to 39B, fading to 38A to 39B; under side 39B. Number of Petals:Four (4). Size: Individual petals are 6 mm in which and 8 mm in length; flower is 15 mm in diameter.

*Reproductive organs:*— Stamens: Eight (8) in number. Anthers: Flat, elliptical, color yellow-green. Filament color: Light green. Pollen Color: Yellow. Pistils: Stigma: Shape flat, mature color is white. Style Color: Green. Ovaries: Four (4) in number, size 6 mm, color green.

*Disease resistance:* Chivalry has shown resistance to powdery mildew. No other disease problems have been noted to date.

*Other important characteristics:* Chivalry is an addition to a series of Kalanchoe cultivars including Majestic, Revelry (U.S. Plant Pat. No. 7,795), Keepsake (U.S. Plant Pat. No. 7,798), Heirloom (U.S. Plant Pat. No. 7,810), Merit (application pending); Empress (application pending), and Legacy (U.S. Plant Pat. No. 9,111) that are matched closely for flowering time, plant height, branching and growth regulator response. This allows the domestic grower to sell all eight colors at the same time from a single planting date and use the same growing methods on each to end up with a uniform crop. The end product is an easier crop for the grower to produce and a higher quality crop for the consumer to buy. All cultivars are ideal for either 10 or 15 cm pot production.

It is claimed:

1. A new and distinct cultivar of Kalanchoe plant named Chivalry, as illustrated and described.

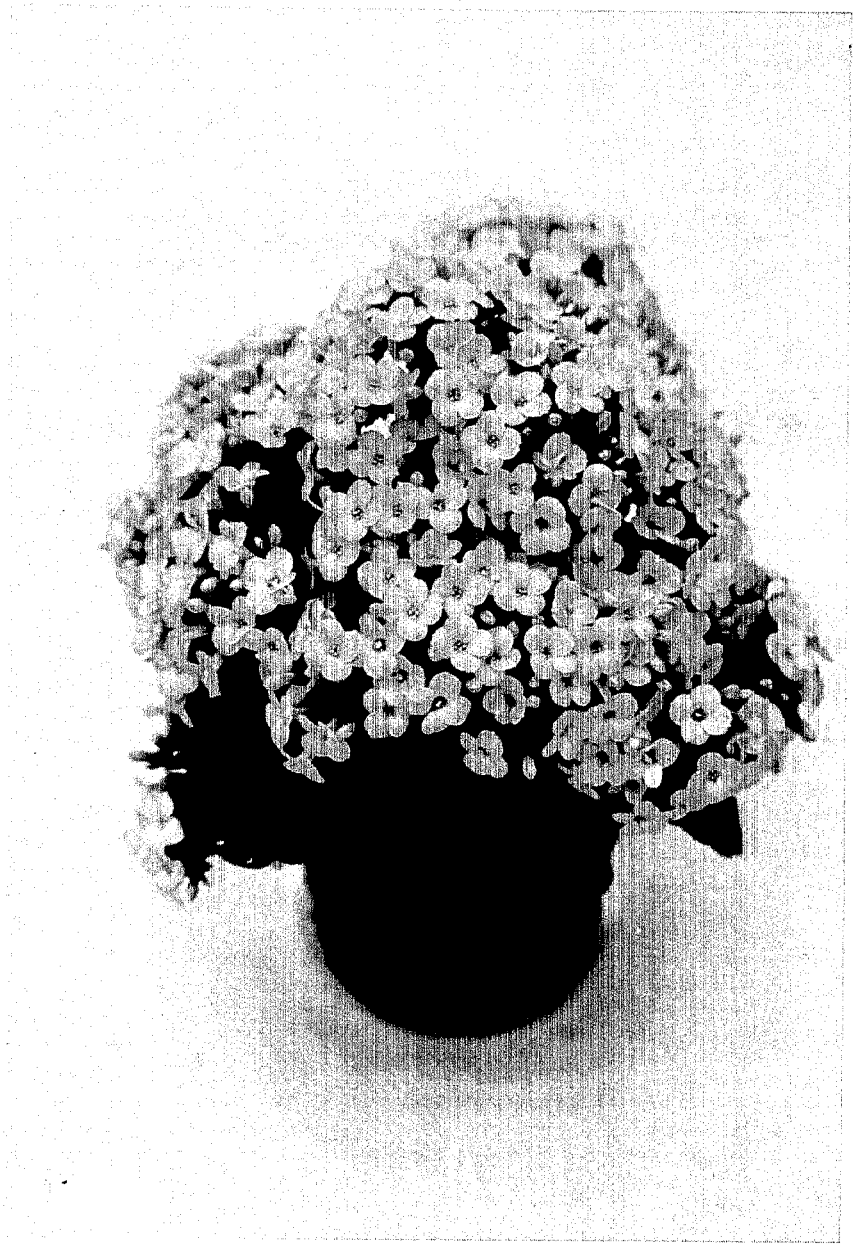

* * * * *